(12) United States Patent
Hoshino et al.

(10) Patent No.: US 7,980,702 B2
(45) Date of Patent: Jul. 19, 2011

(54) IMAGE DISPLAY DEVICE

(75) Inventors: Hiroshi Hoshino, Hirakata (JP); Ryo Kawamura, Katsushika (JP); Atsuyuki Yamamoto, Sakai (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 447 days.

(21) Appl. No.: 12/299,766

(22) PCT Filed: Feb. 8, 2007

(86) PCT No.: PCT/JP2007/052665
§ 371 (c)(1),
(2), (4) Date: Nov. 5, 2008

(87) PCT Pub. No.: WO2007/141533
PCT Pub. Date: Dec. 13, 2007

(65) Prior Publication Data
US 2009/0190097 A1    Jul. 30, 2009

(30) Foreign Application Priority Data

Jun. 8, 2006    (JP) ................................. 2006-160144

(51) Int. Cl.
*G03B 21/14* (2006.01)
*G03B 21/28* (2006.01)
*G03B 21/26* (2006.01)
*G03B 21/56* (2006.01)
*H04N 13/04* (2006.01)
*G02B 27/14* (2006.01)
*G02B 5/10* (2006.01)

(52) U.S. Cl. .............. 353/69; 353/119; 353/98; 353/37; 353/79; 353/7; 353/10; 348/51; 359/451; 359/631; 359/853; 359/867; 359/869

(58) Field of Classification Search .................. 353/119, 353/69, 98, 37, 79, 7, 10; 348/51; 359/451, 359/631, 853, 867, 869
See application file for complete search history.

(56) References Cited

U.S. PATENT DOCUMENTS

| 4,395,010 A | 7/1983 | Helgeland et al. |
| 4,634,384 A * | 1/1987 | Neves et al. .................... 434/44 |
| 4,717,248 A | 1/1988 | LaRussa |

(Continued)

FOREIGN PATENT DOCUMENTS

DE    38 24 187 A1    1/1990

(Continued)

OTHER PUBLICATIONS

Taiwanese Office Action for the Application No. 096105121 dated Nov. 1, 2010.

(Continued)

*Primary Examiner* — Georgia Y Epps
*Assistant Examiner* — Magda Cruz
(74) *Attorney, Agent, or Firm* — Cheng Law Group, PLLC (57) ABSTRACT

An image display device of the present invention comprises projectors, a reflecting mirror, a screen, an image signal processor which performs a distortion correction, and a base for supporting the projectors, the reflecting mirror, and the screen. The projectors, reflecting mirror, and screen are assembled in one to constitute a single moving unit, and the image display device further comprises a lifting device capable of moving the moving unit in a vertical direction with respect to the base.

15 Claims, 6 Drawing Sheets

U.S. PATENT DOCUMENTS

| | | | |
|---|---|---|---|
| 5,348,324 A | 9/1994 | Trotta | |
| 5,833,340 A | 11/1998 | Yoshikawa et al. | |
| 6,003,995 A * | 12/1999 | Dugdale et al. | 353/98 |
| 6,297,814 B1 | 10/2001 | Masuda et al. | |
| 6,390,627 B1 | 5/2002 | Kuroda | |
| 6,985,765 B2 | 1/2006 | Morita et al. | |
| 7,766,483 B2 * | 8/2010 | Balu et al. | 353/7 |
| 2003/0218720 A1 | 11/2003 | Morita et al. | |

FOREIGN PATENT DOCUMENTS

| | | |
|---|---|---|
| JP | 55-050792 A | 4/1980 |
| JP | 63-149971 A | 6/1988 |
| JP | 02-196230 A | 8/1990 |
| JP | 03-027085 A | 2/1991 |
| JP | 03-080479 U | 8/1991 |
| JP | 06-016952 U | 3/1994 |
| JP | 08-129341 A | 5/1996 |
| JP | 09-065260 A | 3/1997 |
| JP | 11-090041 A | 4/1999 |
| JP | 2000-350230 A | 12/2000 |
| JP | 2002-148711 A | 5/2002 |
| JP | 2002-244212 A | 8/2002 |
| JP | 3387487 B2 | 3/2003 |
| JP | 2003-177469 A | 6/2003 |
| JP | 2003-233031 A | 8/2003 |
| TW | 425490 | 3/2001 |

OTHER PUBLICATIONS

International Search Report for the Application No. PCT/JP2007/052665 mailed Jul. 31, 2007.

Notification of Reasons for Refusal for the Application No. JP2007-029271 from Japan Patent Office mailed Jul. 8, 2008.

* cited by examiner

Fig. 7

IMAGE DISPLAY DEVICE

TECHNICAL FIELD

The present invention relates to an image display device which displays an image on a screen.

BACKGROUND ART

Japanese Patent Publication No. 3387487 discloses an image display device which displays an image on a large screen and thereby can give a realistic image to an observer. The image display device can give an immersion feeling to the observer by providing an image capable of covering the observer's view. Such an image display device, which can not only simply display an image to an observer but also give more natural vision, such as wide field of view, stereoscopic vision, or full-size vision, is required in many fields.

By the way, in such an above image display device, there was a request that a user wants to adjust the height of the screen according to the user's height or uses thereof. However, in the above image display device, because the position of the screen is fixed, it was not possible to adjust the height of the screen according to the user's height or the uses thereof.

DISCLOSURE OF THE INVENTION

In view of the above problem, the object of the present invention is to provide an image display device which can adjust the height of the screen according to a user's height or variety of uses of the image display device.

The image display device of this embodiment comprises an image projection means which receives an image signal and outputs an image, a reflecting mirror which reflects the image outputted from the image projection means, an image display means having an arbitrarily-shaped projection plane on which the image reflected by the reflecting mirror is projected, an image signal processing means which performs a distortion correction to the image signal to be inputted into the image projection means so that the image can be displayed on the projection plane without distortion, and a base for supporting at least the image projection means, the reflecting mirror, and the image display means. The feature of the present invention resides in that the image projection means, the reflecting mirror, and the image display means are assembled in one to constitute a moving unit, and the image display device further comprises a lifting means capable of moving the moving unit in a vertical direction with respect to the base.

In the image display device of the present invention, because the lifting means can move the moving unit in the vertical direction with respect to the base, it is possible to adjust a height of the image display means (namely, a screen) according to a user's height and variety of uses of the image display device, and so on. Furthermore, because the image projection means, the reflecting mirror, and the image display means are assembled in one and constitute a single moving unit, the positional relation among the image projection means, the reflecting mirror, and the image display means is not changed even when the height of the moving unit is changed, whereby the image display device always can display an image with no distortion on the image display means regardless of the height of the moving unit.

Or, the image display device of the present invention may comprise an image projection means which receives an image signal and outputs an image, an image display means having an arbitrarily-shaped projection plane on which the image outputted from the image projection means is projected, an image signal processing means which performs a distortion correction to the image signal to be inputted into the image projection means so that the image can be displayed on the projection plane without distortion, and a base for supporting at least the image projection means and the image display means, and the image projection means and the image display means may be assembled in one to constitute a single moving unit, and the image display device may further comprise a lifting means capable of moving the moving unit in a vertical direction with respect to the base.

In this case, too, the moving unit can be moved by the lifting means in the vertical direction with respect to the base. Furthermore, because the image projection means and the image display means are assembled in one and constitute the single moving unit, the positional relation between the image projection means and the image display means is not changed even when the height of the moving unit is changed, whereby the image display device always can display an image having no distortion on the image display means regardless of the height of the moving unit.

Preferably, in a x-y coordinate with an x-axis and a y-axis which are defined so that the x-axis is along a line of sight of an observer when looking at said image display means horizontally and the y-axis is along the vertical direction, the reflecting mirror is installed so that a position $(x_M, y_M)$ of a lower end of the reflecting mirror meets the following equation:

$$(y_i - y_o) x_M - (x_i - x_o) y_M \leq x_o y_i - x_i y_o \quad \text{(eq.)}$$

where $x_o$ and $y_o$ are x, y coordinates of a predetermined view point of the observer, and $x_i$ and $y_i$ are x, y coordinates of a position of an upper end of the projection plane of said image display means.

In this case, the observer can see the whole area of the projection plane from the predetermined view point without being blocked by the reflecting mirror.

Preferably, the moving unit is configured to be tiltable with respect to the base about an axis which is perpendicular to the vertical direction of the image display unit and is parallel to an aperture plane of the projection plane. In this case, the user can adjust not only the height of the moving unit but also an angle of the moving unit.

It is also preferable that the moving unit is configured to be rotatable with respect to the base about an axis which is along the vertical direction of the image display unit.

Preferably, the image projection means has a left-eye projector for outputting an image for a left eye and a right-eye projector for outputting an image for a right eye to display a three-dimensional image on the image display means.

Preferably, the image projection means, the reflecting mirror, and the image display means are assembled in one using a mounting member, and the mounting member is a generally rectangular parallelepiped having a concave portion in one side surface, and the image display means has a concave projection plane, and the concave projection plane is disposed in the concave portion of the mounting member. In this case, the image display means does not project from the mounting member, whereby the image display device can be downsized.

In the above case, it is preferable that the base has a box-shaped housing having an opened upper surface, and a lower part of the mounting member is housed in the housing so as to be freely moved up and down. In this case, it is possible to support the mounting member with stability by housing the mounting member in the box-shaped housing.

Preferably, the base is provided with a handrail and wheels so as to be movable. In this case, a user can easily move the image display device by gripping the handrail and pushing the base.

BEST MODE FOR CARRYING OUT THE INVENTION

Hereinafter, the present invention will be described in more detail with reference to the accompanying drawings.

First Embodiment

Figure 1:
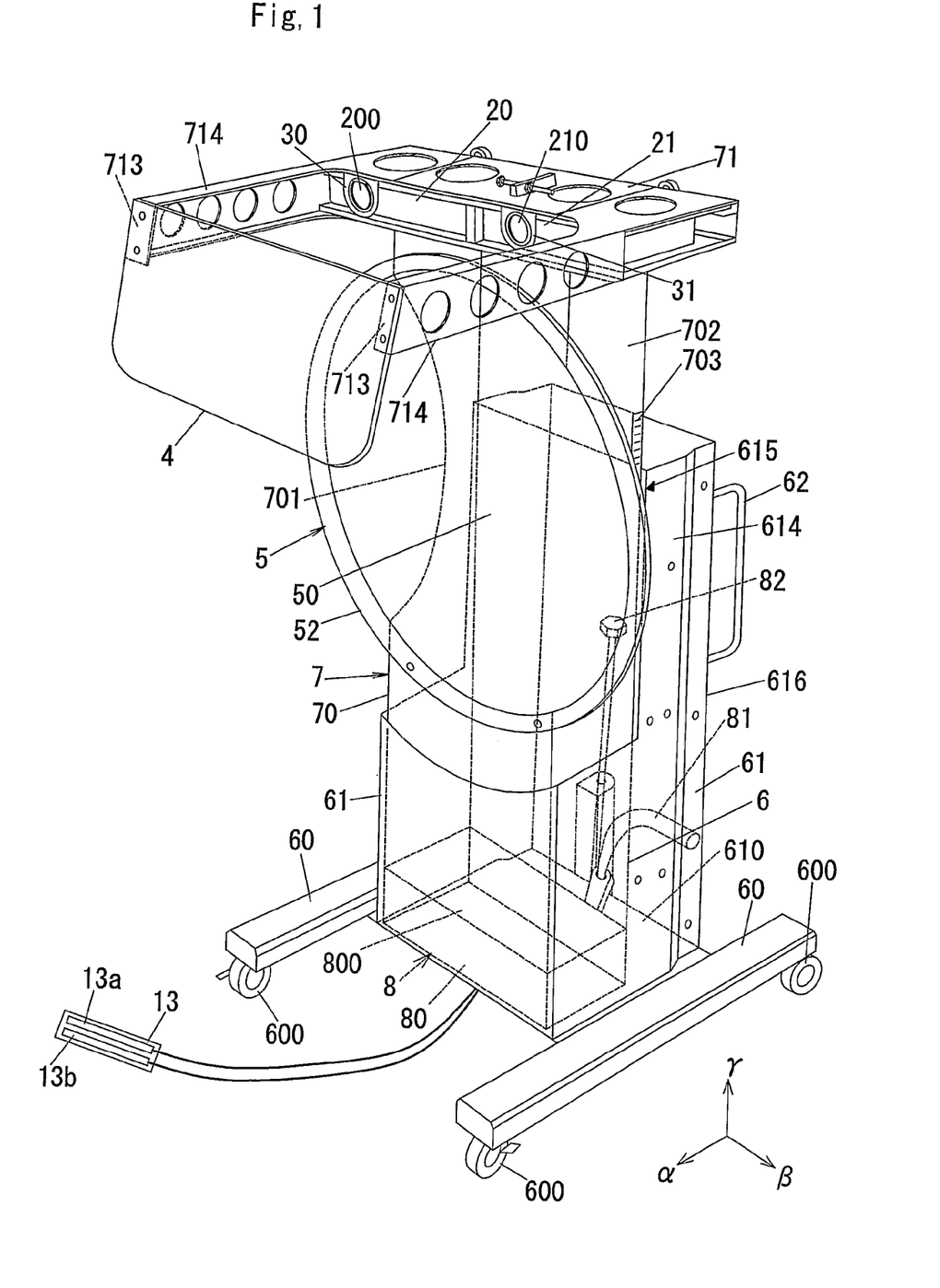
FIG. 1 is a perspective view of an image display device in accordance with a first embodiment of the present invention.

FIG. 1 shows an image display device in accordance with a first embodiment of the present invention. The image display device is connected with an external camera 13, and displays an image taken by the camera 13 on a screen in three dimensions without distortion, and an observer can perform various works while observing the image taken by the camera 13 on the screen.

In this embodiment, in order to display a 3-D image on the screen, the camera 13 comprises a left-eye camera 13a for taking an image for a left eye and a right-eye camera 13b for taking an image for a right eye, and the left-eye camera 13a and the right-eye camera 13b are aligned parallel to each other in a housing. The camera 13 may have only one camera when two-dimensional image is displayed on the screen.

This image display device comprises projectors 20 and 21 (image projection means) each of which receives an image signal and outputs an image, a reflecting mirror 4 which reflects the images outputted from the projectors 20 and 21, a screen 5 (an image display means) having a projection plane 50 in a form of a hemisphere dome on which the images reflected by the reflecting mirror 4 are projected, an image signal processor 1 (see FIG. 3) which is connected to the cameras 13a, 13b and performs a distortion correction to the image signal to be inputted into the projectors 20 and 21 so that the images can be displayed on the projection plane 50 without distortion, a base 6 for supporting the projectors 20 and 21, the reflecting mirror 4, and the screen 5, and a lifting device 8 capable of moving the projectors 20 and 21, the reflecting mirror 4, and the screen 5 assembled in one as described in detail later in a vertical direction with respect to the base 6.

The image signal processor 1 is constituted by e.g. a personal computer, and has a left-eye image corrector 10 (see FIG. 3) for correcting the image signal for a left eye, a right-eye image corrector 12 (see FIG. 3) for correcting the image signal for a right eye, and a controller 10 (see FIG. 3) for synchronizing and controlling the left-eye image corrector and the right-eye image corrector.

Figure 3:
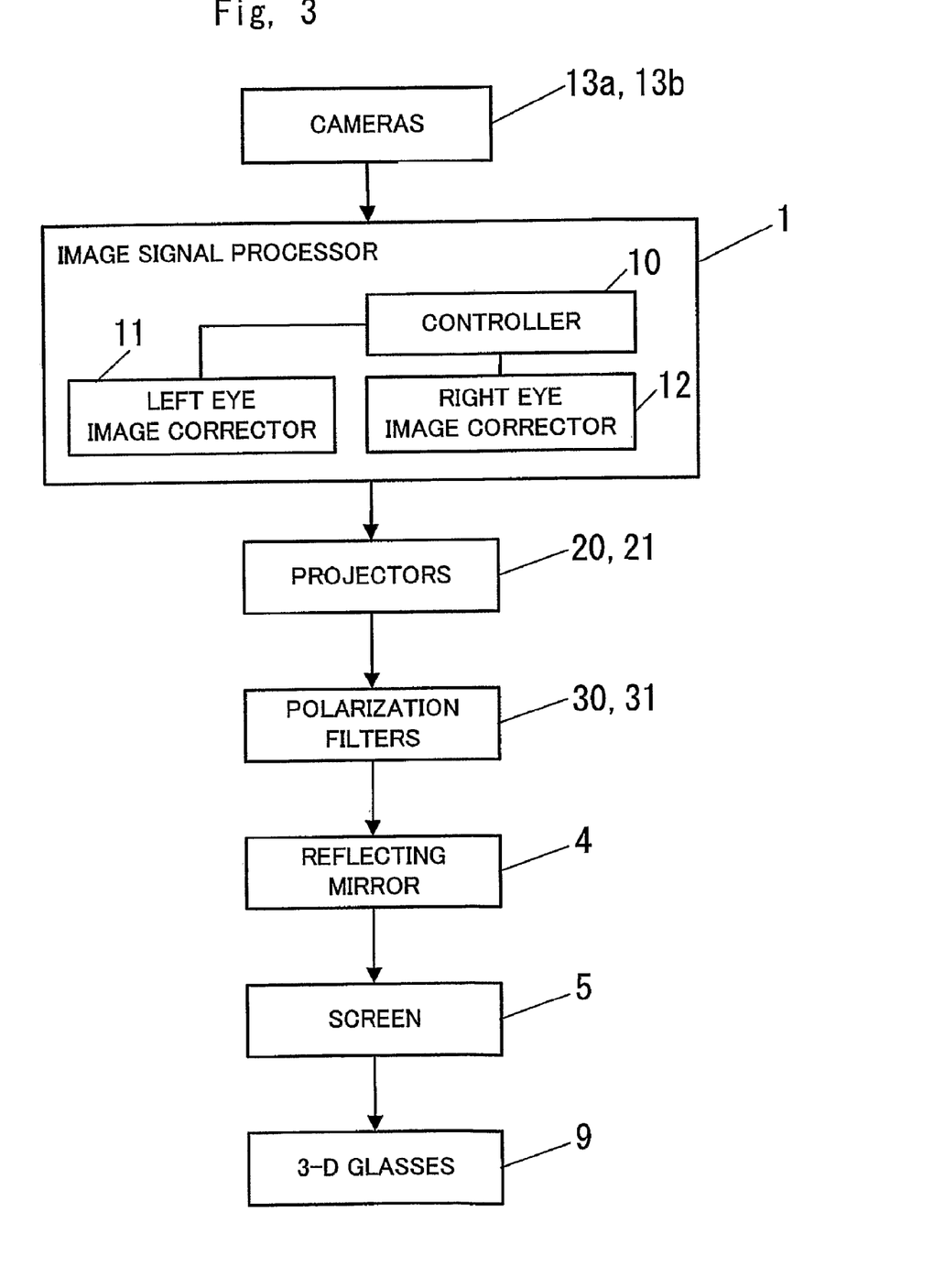
FIG. 3 is a block diagram showing a constitution of the image display device of FIG. 1.

The left-eye image corrector 11 is connected to the left-eye camera 13a, and calculates correction parameters to the image signal for a left eye so that the image for a left eye can be displayed on the curved screen 5 with no distortion, and it corrects the image for a left eye based on the correction parameters. In other words, the left-eye image corrector 11 gives distortions to the image for a left eye in advance so that the image with no distortion and no deformation can be displayed on the screen 5.

The right-eye image corrector 12 is connected to the right-eye camera 13b, and, as is the case with the left-eye image corrector, it calculates correction parameters to the image signal for a right eye so that the image for a right eye can be displayed on the curved screen 5 without distortion, and corrects the image signal for a right eye based on the correction parameters. In other words, the right-eye image corrector 12 gives distortions to the image for right eye image in advance so that the image with no distortion and no deformation can be displayed on the screen 5.

One projector (a left-eye projector) 20 is connected to the left-eye image corrector 11, and receives the image signal for a left eye corrected by the left-eye image corrector 11, and outputs the image for a left eye from a lens 200, and the other projector (a right-eye projector) 21 is connected to the right-eye image corrector 12, and receives the image signal for a right eye corrected by the right-eye image corrector 12, and outputs the image for a right eye from a lens 210.

In addition, a left-eye polarization filter 30 is attached to the lens 200 and a right-eye polarization filter 31 is attached to the lens 210. The left-eye polarization filter 30 and the right-eye polarization filter 31 allow circularly-polarized lights which are different from each other to pass through the filters. The image for a left eye outputted from the left-eye projector 20 passes through the left-eye polarization filter 30 and the image for a right eye outputted from the right eye projector 21 passes through the right-eye polarization filter 31. It is not limited that each polarization filter allows circularly-polarized light to pass through the filter, but each polarization filter 30, 31 may allow linearly-polarized light to pass through the filter. For example, the left-eye polarization filter 30 may allow linearly-polarized light of vertical direction to pass through the filter, and the right-eye polarization filter 31 may allow linearly-polarized light of horizontal direction to pass through the filter.

The reflecting mirror 4 is installed above a view of the observer, and it reflects the images for a left eye and a right eye outputted from the left-eye projector 20 and the right-eye projector 21 to the projection plane 50 of the screen 5.

The projection plane 50 of the screen 5 has a hemisphere dome shaped configuration as mentioned above, and is coated with a coating material having specular effect, such as silver coating. The screen is a so-called silver screen. The shape of the screen 5 is not limited to the hemisphere dome shape, but it may be a compound screen including a flat surface and a quadratic surface. Even if the screen 5 has such a shape, an image having no distortion can be displayed on the screen by the image signal processor. In addition, the screen 5 of FIG. 1 has a flange (a frame) 52 around its outer circumference, and the projection plane 50 in the form of the hemisphere dome is formed inside the flange 52.

The projectors 20 and 21, the reflecting mirror 4, and the screen 5 are assembled in one using a mounting member 70 to constitute a single moving unit 7.

In more detail, the mounting member 70 is a generally rectangular parallelepiped, and is formed from a metal plate, and has a concave portion 701 in one side surface on a front side of the image display device (on a positive α-axis direction side in FIG. 1), and has a projector housing 71 on an upper surface thereof. Furthermore, a pair of arms 714 is extended from both sides of the projector housing 71 toward the front side of the image display device.

The projection plane 50 of a concave shape is disposed in the concave portion 701 of the mounting member 70, and the screen 5 is fixed to the mounting member 70. When the screen 5 is fixed to the mounting member 70, an aperture plane of the screen 5 and the front surface of the mounting member 70 become generally one plane. By disposing the screen 5 having the concave projection plane 50 in the concave portion 701, the screen 5 does not project from the mounting member 70, whereby the image display device can be downsized.

The projector housing 71 has a box shape with an opened surface, at least, on the front side of the image display device, and the projectors 20 and 21 are mounted inside the projector housing 71, and the lenses 200 and 201 of the projectors 20 and 21 face the outside through the polarization filters 30, 31 from the opened surface.

The reflecting mirror 4 is fixed on the front ends of the pair of arms 714 at a predetermined angle.

The base 6 is formed into a generally rectangular parallelepiped from a metal plate, and has, on the front surface side thereof, a box-shaped housing 61 having an opened upper surface, and has a pair of legs 60 on the lower end. Each leg 60 is equipped with wheels 600 at the longitudinal opposite ends. Handrails 62 are provided on opposite sides of the back surface of the base 6.

The lower part of the moving unit 7 is housed in the housing 61 so as to be freely moved up and down. By housing the lower part of the moving unit 7 in the box-shaped housing 61, it becomes possible to support the moving unit 7 with stability.

Also, by providing the handrails 62 and the wheels 600 to the base 6, it becomes possible for the user to move the image display device easily by grasping the handrails 62 and pushing the base 6.

In addition, scales 703 are provided on the side surface of the mounting member 70 of the moving unit 7, and a triangle mark 615 is provided on the side surface of the base 6. Therefore, it is possible to measure the height of the moving unit 7 (the screen 5) by the scales 703 and the triangle mark 615.

The lifting device 8 is for lifting the moving unit 7 by e.g. hydraulic pressure, and comprises a driving member 8, a raising step 81, and a lowering lever knob 82. The driving member 8 is disposed on the bottom surface 610 of the housing 61, and the moving unit 7 is fixedly put on the upper surface 800 of the driving member 8. The raising step 81 and the lowering lever knob 82 are provided on the back side 616 of the housing 61. When the user steps on the raising step 81 from top down, the upper surface 800 of the driving member 80 is moved up. When the user steps on the raising step 81 many times, the upper surface 800 is further moved up. On the other hand, when the user rotates the lowering lever knob 82 in anticlockwise direction, the upper surface 800 of the driving member 80 is lowered. When the user rotates the lowering lever knob 82 in clockwise direction, the vertical motion of the upper surface 800 is locked. That is, in this lifting device 8, a user can move up or down the upper surface 800 of the driving member 80 with respect to the base 6 in the vertical direction by operating the raising step 81 and the lowering lever knob 82. By this, the moving unit 7 put on the upper surface 800 of the lifting device 8 can be moved in the vertical direction with respect to the base 6.

It should be noted that because the projectors 20 and 21, the reflecting mirror 4, and the screen 5 are assembled in one to constitute the single moving unit 7 in this embodiment, the positional relation among the projectors 20 and 21, the reflecting mirror 4, and the screen 5 is fixed even when the moving unit 7 is moved by the lifting device 8, so that the image display device always can display an image with no distortion on the screen 5 regardless of the height of the moving unit 7. If the projectors 20 and 21, the reflecting mirror 4, and the screen 5 are not assembled in one, when the height of the screen 5 is changed, the positional relations among the projectors 20 and 21, the reflecting mirror 4, and the screen 5 is also changed, whereby the image may not be displayed at the center of the screen 5, or the image with distortion may be displayed on the screen. Therefore, every time the user changes the height of the screen 5, the user has to adjust the positional relation among the projectors 20 and 21, the reflecting mirror 4, and the screen 5, and therefore the user consumes much of his or her time and energy to adjust the positional relation. While on the other hand, in this embodiment, because the projectors 20 and 21, the reflecting mirror 4, and the screen 5 are assembled in one and constitute the single moving unit 7, the positional relation among them is fixed, so that the image having no distortion can be always displayed on the screen 5 without positional adjustment even when the position of the screen 5 is changed by the lifting device 8.

Figure 2:
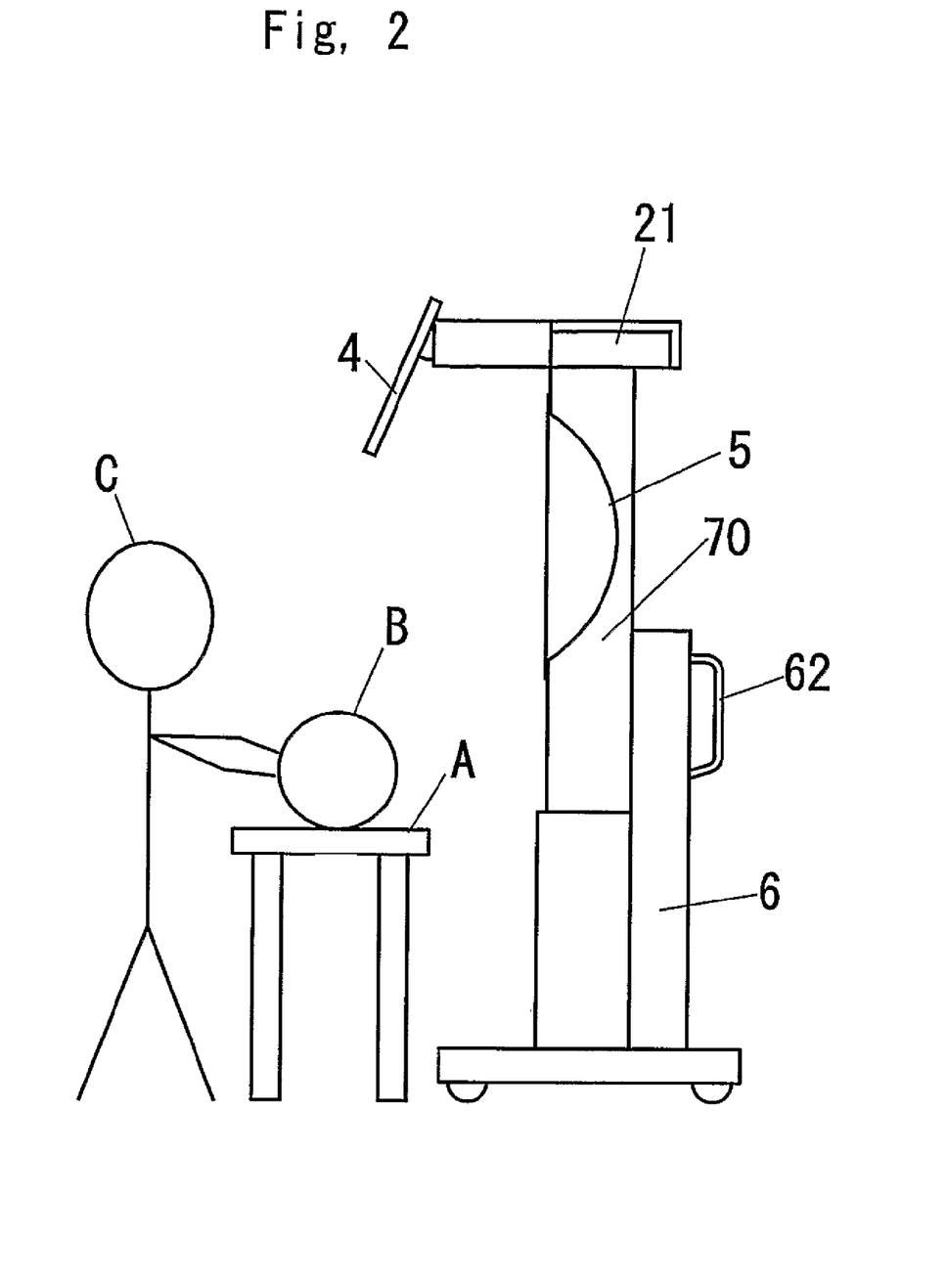
FIG. 2 is a view for explaining a use situation of the image display device of FIG. 1.

Next, the usage method of the image display device of this embodiment will be explained below. As shown in FIG. 2, when a user uses this image display device, a workbench (A) is put in front of the image display device, and a work object (B) is put on the workbench (A). And the camera 13 is placed so that it can take an image of the work object (B) (in FIG. 2, the camera 13 is not shown), and the image that the camera 13 took (namely, the work object (B)) is displayed on the screen 5 in three dimensions. One or more workers (C) can perform an operation to the work object (B) while looking at the image displayed on the screen 5.

For example, the camera 13 is a 3-D endoscope, and a patient (B) is laid down on an operating table (A), and one or more doctors (C) perform an endoscopic operation to the patient (B) while looking at an affected area displayed on the screen 5.

Because the moving unit 7 is movable up and down in the image display device of this embodiment, the worker (C) can adjust the height of the screen 5 to the most easy-to-see position by operating the lifting device 8. At that time, because the positional relation among the projectors 20 and 21, the reflecting mirror 4, and the screen 5 is fixed, the image display device can always display the image having no distortion on the screen 5 even when the moving unit 7 is moved. Furthermore, because the image display device has handrails 62 and wheels 600, it is easy for the worker to move the image display device e.g. from one room to another room by gripping the handrails 62 and pushing the base 6. Furthermore, by lowering the height of the moving unit 7, it becomes easy to get the image display device through e.g. a door of the room.

Next, the operation of this image display device will be explained below with reference to FIG. 3. First, the cameras 13a, 13b take an image of the work object (B). The image signals of the cameras 13a, 13b are inputted into the image signal processor 1, and the left-eye image corrector 11 and the right-eye image corrector 12 each perform a distortion correction to each image signal so that the image can be displayed on the screen 5 without distortion. The left-eye image corrector 11 and the right-eye image corrector 12 are controlled by the controller 10 in synchronization with each other, and the corrected image signals are outputted to the projectors 20 and 21. The projectors 20 and 21 receive the image signals for a left eye and the image signal for a right eye, respectively, and output an image for a left eye and an image for a right eye, respectively. The images outputted from the projectors 20 and 21 pass through the left-eye polarization filter 30 and the right-eye polarization filter 31, and are reflected by the reflecting mirror 4, and are projected on the projection plane 50 of the screen 5. When the worker looks at the screen 5, he or she wears stereoscopic glasses 9. The stereoscopic glasses 9 has a polarization filter having the same polarization manner as the left-eye polarization filter 30 at a left eye part, and has a polarization filter having the same polarization manner as the right-eye polarization filter 31 at a right eye part. By seeing the image displayed on the screen 5 through the stereoscopic glasses 9, the worker can see a stereoscopic image.

As mentioned above, in the image display device of this embodiment, a user can adjust the height of the screen 5 according to the user's height and the uses of the image display device, and furthermore, even when the height of the screen is changed, the image display device can always display an image with no distortion on the screen 5.

Figure 4:
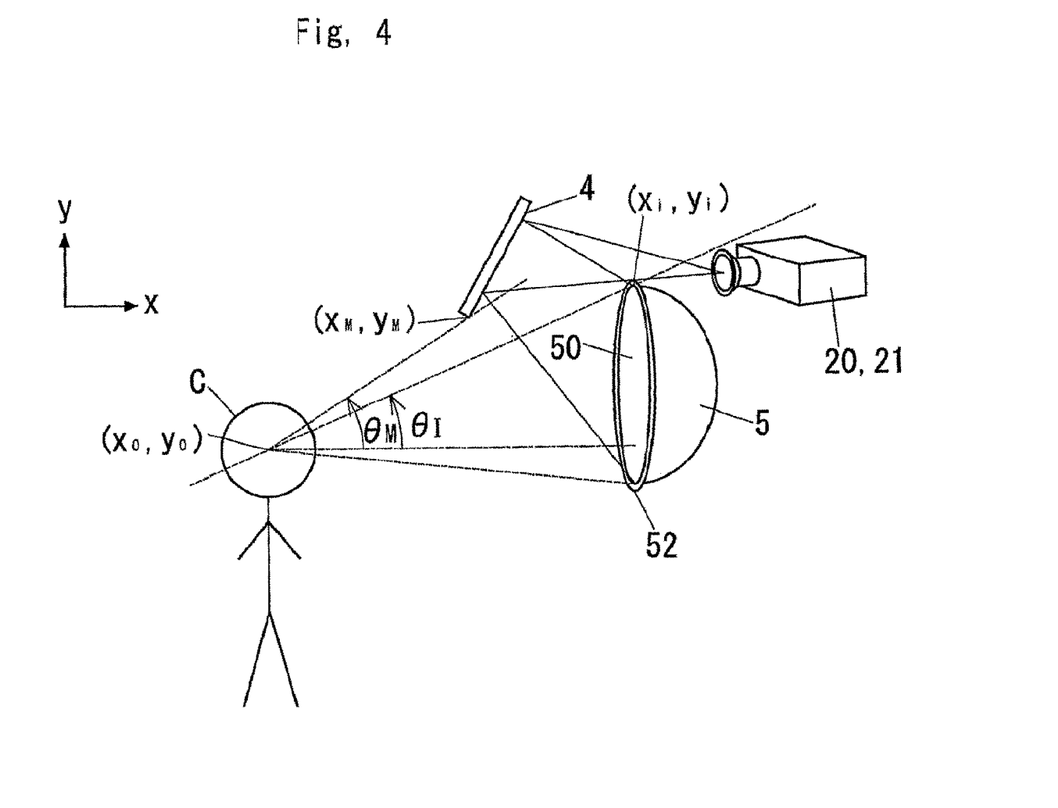
FIG. 4 is a view for explaining an installation position of a reflecting mirror of the image display device of FIG. 1.

By the way, in this embodiment, the images outputted from the projectors 20 and 21 are reflected to the screen 5 by the reflecting mirror 4. In the case where the reflecting mirror 4 is provided, it is not necessary to arrange the projectors and the screen in a line, whereby it is possible to downsize the image display device. However, when the reflecting mirror 4 is provided, the reflecting mirror 4 may come into the view of the observer, and it may block the observer's view. Therefore, as shown in FIG. 4, when using the reflecting mirror 4, it is preferable that, in a x-y coordinate with an x-axis and a y-axis which are defined so that the x-axis is along a line of sight of an observer C when looking at the screen 5 (the image display means) horizontally and the y-axis is along the vertical direction, the reflecting mirror 4 is installed so that a position ($x_M$, $y_M$) of a lower end of the reflecting mirror 4 meets the following equation:

$$(y_i - y_0)x_M - (x_i - x_0)y_M \leq x_0 y_i - x_i y_o$$ (eq.)

where $x_o$ and $y_o$ are x, y coordinates of a predetermined view point of the observer C, and $x_i$ and $y_i$ are x, y coordinates of a position of an upper end of projection plane 50 of the screen 5 ($x_i$ and $y_i$ are the upper end of projection plane 50, not the upper end of the flange 52 of the screen 5. That is, $x_i$ and $y_i$ are the upper end of an effective projection plane of the screen 5.).

The above equation shows a region where an angle $\theta_M$, at which the observer C looks at the lower end of the reflecting mirror 4 from the predetermined view point ($x_o$, $y_o$), is larger than an angle $\theta_1$, at which the observer C looks at the upper end of the projection plane 50 of the screen 5 from the predetermined view point ($x_o$, $y_o$) (that is, the above equation shows a region where $\theta_M \geq \theta_1$). Therefore, when the reflecting mirror 4 is installed so that the position ($x_M$, $y_M$) of the lower end of the reflecting mirror 4 satisfies the above equation, the observer C can see the whole area of the projection plane 50 without being blocked by the reflecting mirror 4.

Although, in this embodiment, the images outputted from the projectors 20 and 21 are projected on the screen 5 through the reflecting mirror 4, the projectors 20 and 21 may be disposed on the front side of the arms 714 so that they can face the screen 5, and the images outputted from the projectors 20 and 21 may be projected on the screen 5 directly. That is, the image device of this embodiment may comprise projectors 20 and 21, a screen 5, image signal processor 1, and the base 6 for supporting the projectors 20 and 21 and the screen 5, and the projectors 20 and 21 and the screen 5 may be assembled in one to constitute a single moving unit (not shown), and the lifting device 8 may move the moving unit in the vertical direction. The constitutions of the image signal processor 1 and the base 6 are the same with the image display device of FIG. 1. In this case, too, because the moving unit can be lifted, a user can adjust the height of the screen 5 to the most easy-to-see position by operating the lifting device 8. And furthermore, because the positional relation between the projectors 20, 21 and the screen 5 is fixed, the image display device can always display an image with no distortion on the screen 5, even if the moving unit is moved. Furthermore, in this case, too, it is preferable that the screen 5 is disposed in the concave portion of the mounting member and the mounting member is housed in the box-shaped housing 61 so as to be freely moved up and down.

Second Embodiment

Figure 5:
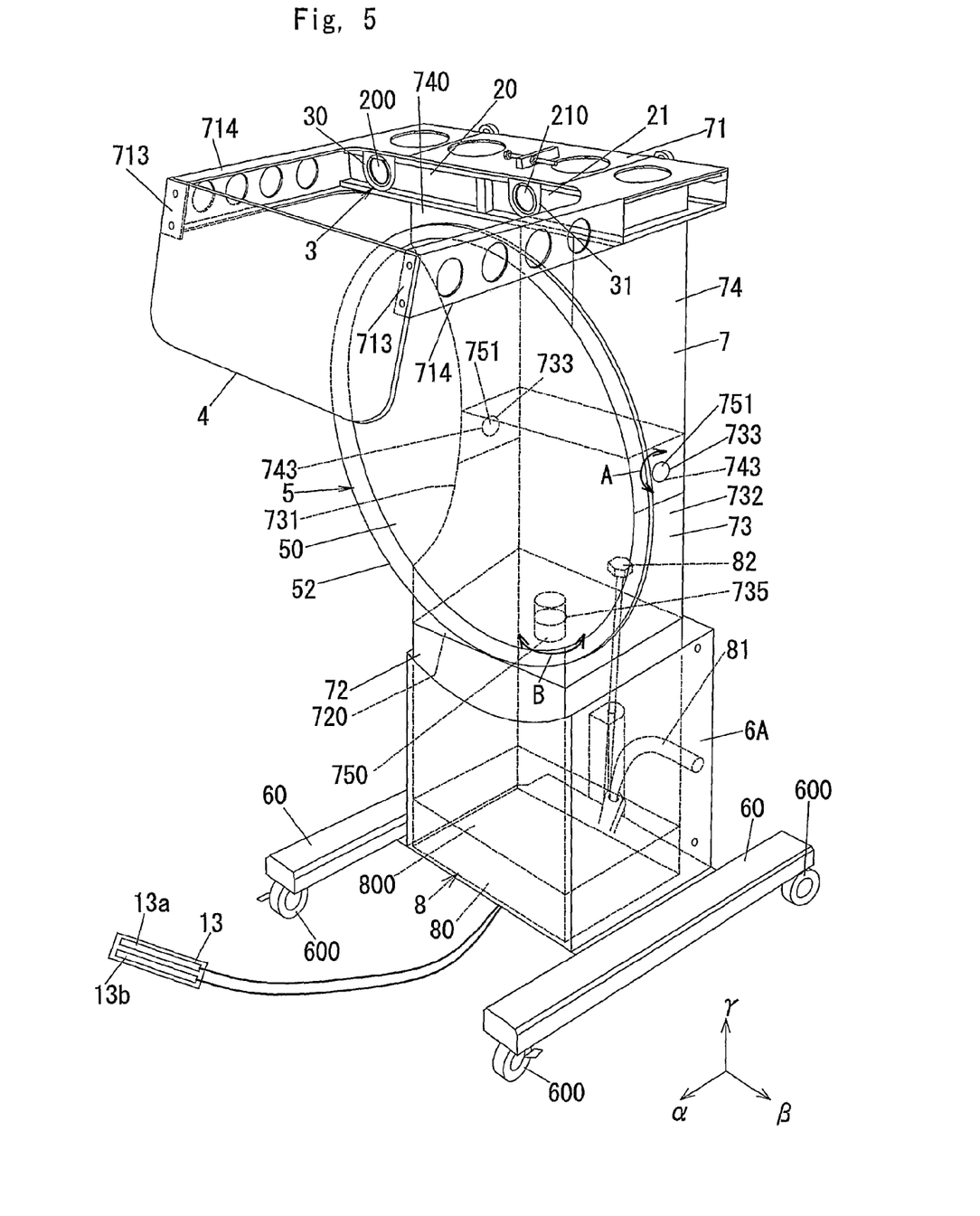
FIG. 5 is a perspective view of an image display device in accordance with a second embodiment of the present invention.

FIG. 5 shows an image display device in accordance with a second embodiment of the present invention. The basic composition of this embodiment, except for the mounting member 70 and the base 6, is identical to the first embodiment, so similar parts to the first embodiment are identified by the same reference character and no duplicate explanation is made here.

The image display device of this embodiment is configured to be tiltable with respect to the base 6A about an axis which is perpendicular to the vertical direction of the image display unit and is parallel to an aperture plane of the projection plane 50 (that is, about a β-axis in FIG. 5) and to be rotatable with respect to the base 6A about an axis which is along the vertical direction of the image display device (that is, about a γ-axis in FIG. 5), as well as to be liftable in the vertical direction.

The base 6A of this embodiment is formed into a box shape having an opened upper surface, and, as is the case with the first embodiment, it has wheels 600 on each leg 60.

The mounting member of this embodiment comprises a lower mounting member 72, a middle mounting member 73, and an upper mounting member 74.

The lower mounting member 72 is formed into a box shape from e.g. a metal plate, and is housed in the base 6A so as to be freely moved up and down. As is the case with the first embodiment, the driving member 80 of the lifting device 8 is disposed between the lower mounting member 72 and the bottom of the base 6A. A cylindrical shaft 750 is projected from the center of the upper surface 720 of the lower mounting member 72.

The middle mounting member 73 is formed from e.g. a metal plate, and has a through hole 735 in the bottom surface, and is disposed on the lower mounting member 72 so that the shaft 750 of the lower mounting member 72 penetrates the through hole 735. By this, the middle mounting member 73 can rotate with respect to the lower mounting member 72 in a direction of an arrow B of FIG. 5. The middle mounting member 73 also has through holes 733 in an upper part of each side surface 732 in the Y-axis direction of FIG. 5

The upper mounting member 74 is formed from e.g. a metal plate, and has through holes 743 in a lower part of each side surface in the Y-axis direction of FIG. 5. The upper mounting member 74 is disposed so that the lower part of the upper mounting member 74 overlaps the upper part of the middle mounting member 73, and the position of each through hole 743 of the upper mounting member 74 corresponds with the position of each through hole 733 of the middle mounting member 73. Then, a bolt 751 is inserted into each through hole 743, 733, whereby the upper mounting member 74 becomes tiltable with respect to the middle mounting member 73 about the bolt 751 (that is, the upper mounting member 74 becomes tiltable in a direction of an arrow A of FIG. 5).

A concave portion 731 for disposing the screen 5 is formed astride the front surface (a surface on the positive α-axis direction side in FIG. 5) of the upper mounting member 74 and the front surface of the middle mounting member 73. The screen 5 is disposed in the concave portion 731, and it is not fixed to the middle mounting member 73, and is fixed to only the upper mounting member 74. A specified space is created between the back surface of the screen 5 and the concave portion 731 so that interference does not occur between the back surface of the screen 5 and the concave portion 731 when the upper mounting member 74 is tilted toward the middle mounting member 73.

As is the case with the first embodiment, the projector housing 71 is provided on the upper part of the upper mounting member 74, and the projectors 20 and 21 and the reflecting mirror 4 are fixed to the upper mounting member 74. That is, in this embodiment, the projectors 20 and 21, the reflecting mirror 4, and the screen 5 are assembled in one using the upper mounting member 74, and constitute the single moving unit 7.

In the image display device of this embodiment constituted as above, when the lifting device 8 lifts or lowers the lower mounting member 72, the moving unit 7 is moved in the vertical direction with respect to the base 6A through the lower mounting member 72 and the middle mounting member 73. Therefore, a user can move the moving unit 7 in the vertical direction with respect to the base 6A by operating the lifting device 8. Furthermore, the user can tilt the moving unit 7 with respect to the base 6A about an axis which is perpendicular to the vertical direction of the image display unit and is parallel to the aperture plane of the projection plane 50 (that is, about the β-axis in FIG. 5) by tilting the upper mounting member 74 with respect to the middle mounting member 73 by hand or electromotion. Still furthermore, the user can rotate the moving unit with respect to the base 6A about an axis which is along the vertical direction of the image display unit (that is, about the γ-axis in FIG. 5), by rotating the middle mounting member 73 with respect to the lower mounting member 72. Because the positional relation among the projectors 20 and 21, the reflecting mirror 4, and the screen 5 is fixed, this image display device can always display the image having no distortion on the screen 5 even when the moving unit 7 is moved and/or tilted and/or rotated with respect to the base 6A.

As mentioned above, in the image display device of this embodiment, because the user can not only move the moving unit 7 in the vertical direction but also tilt and rotate it with respect to the base 6A, the user can adjust the height and the angle of the screen more minutely according to the user's height or variety of uses or a user's location.

In this embodiment, too, the projectors 20, 21 may be disposed on the front side of the arms 714 so that they face the screen 5, and the image outputted from the projectors may be projected on the screen 5 directly.

Third Embodiment

Figure 6:
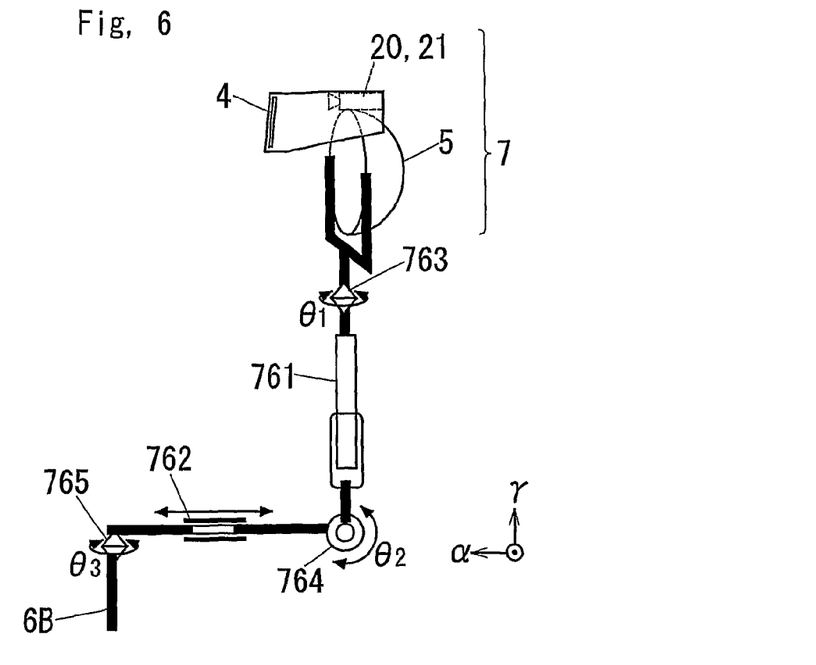
FIG. 6 is a view showing, schematically, an image display device in accordance with a third embodiment of the present invention.

FIG. 6 shows, schematically, a constitution of an image display device in accordance with a third embodiment of the present invention. The basic composition of this embodiment is identical to the first and second embodiments, so similar parts to these embodiments are identified by the same reference character and no duplicate explanation is made here.

As is the case with the first and second embodiments, in the image display device of this embodiment, the projectors 20 and 21, the reflecting mirror 4, and the screen 5 are assembled in one, and constitute the moving unit 7.

The base 6B of this embodiment is fixed to the ground (not shown) at its one end, and is provided with two rotating mechanisms 763 and 765, a lifting mechanism 761, a tilting mechanism 764, and an expanding mechanism 762 between the moving unit 7 and the base 6B.

The first rotating mechanism 763 is installed between the moving unit 7 and the lifting mechanism 761, and it can rotate the moving unit 7 in a direction of $\theta_1$ of FIG. 6 with respect to the lifting mechanism 761.

The lifting mechanism 761 is installed between the first rotating mechanism 763 and the tilting mechanism 764, and it can move the moving unit up and down through the first rotating mechanism 763 with respect the tilting mechanism 764.

The tilting mechanism 764 is installed between the lifting mechanism 761 and the expanding mechanism 762, and it can tilt the moving unit 7 through the lifting mechanism 761 and the first rotating mechanism 763, in a direction of $\theta_2$ of FIG. 6 with respect to the expanding mechanism 762.

The expanding mechanism 762 is installed between the tilting mechanism 764 and the second rotating mechanism 765, and it can move the moving unit 7 through the tilting mechanism 764, the lifting mechanism 761, and the first rotating mechanism 763 in a direction along the a-axis of FIG. 6 with respect to the second rotating mechanism 765.

The second rotating mechanism 765 is installed between the expanding mechanism 762 and the one end of the base 6B, and it can rotate the moving unit 7 through the expanding mechanism 762, the tilting mechanism 764, the lifting mechanism 761, and the first rotating mechanism 763 in a direction of $\theta_3$ of FIG. 6 with respect to the one end of the base 6B.

That is, the image display device of this embodiment can move the moving unit 7 in the vertical direction, and tilt and rotate the moving unit 7 with respect to the base 6B by the two rotating mechanisms 763 and 765, the lifting mechanism 761, the tilting mechanism 764, and the expanding mechanism 762. Because the positional relation among the projectors 20 and 21, the reflecting mirror 4, and the screen 5 is fixed, the image display device of this embodiment can always display an image with no distortion on the screen 5, no matter how the moving unit 7 is moved.

As is the case with the second embodiment, in the image display device of this embodiment, because a user can not only move the moving unit 7 in the vertical direction but also tilt and rotate it, the user can adjust the height and the angle of the screen more minutely according to the user's height or variety of uses or the user's location.

The combination of the rotating mechanism, the tilting mechanism, and the expanding mechanism is not limited to FIG. 6, but many deformations can be made. For example, in FIG. 7, additional two rotating mechanisms 766 and 767 are installed, and the lifting mechanism 761 is eliminated.

Figure 7:
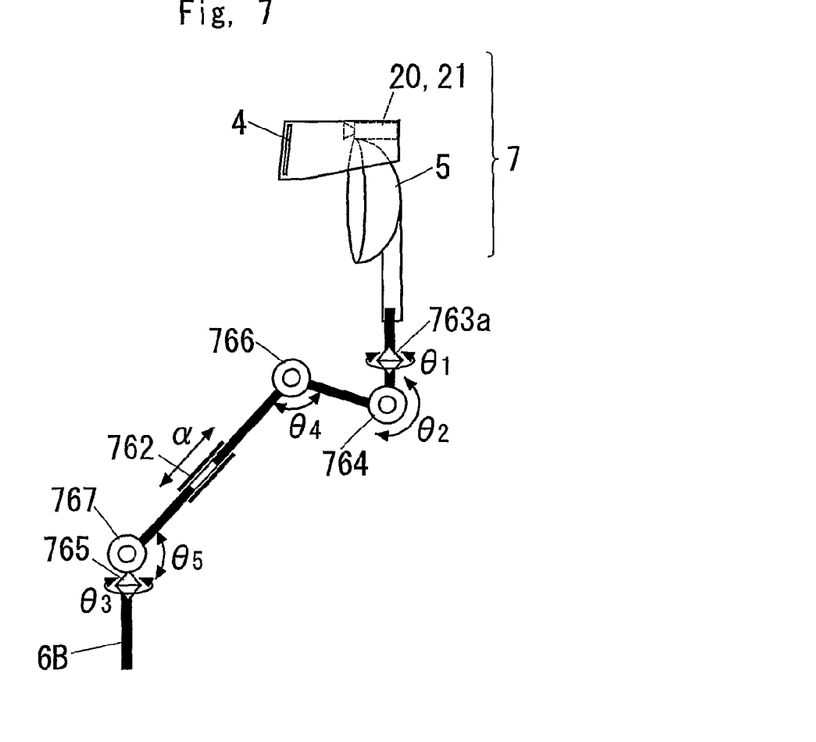
FIG. 7 is a view showing a modified form of the image display device of FIG. 6.

The third rotating mechanism 766 is provided between the expanding mechanism 762 and the first rotating mechanism 764, and it can rotate the first rotating mechanism 764 in a direction of $\theta_4$ of FIG. 7 with respect to the expanding mechanism 762.

The forth rotating mechanism 767 is provided between the expanding mechanism 762 and the second rotating mechanism 765, and it can rotate the expanding mechanism 762 in a direction of $\theta_5$ of FIG. 7 with respect to the second rotating mechanism 765.

In this image display device, the moving unit 7 can be moved up and down with respect to the base 6B by the rotation of the forth rotating mechanism 767 and the expansion of the expanding mechanism 762. That is, the forth rotating mechanism 767 and the expanding mechanism 762 constitute a lifting means capable of moving the moving unit in the vertical direction with respect to the base 6B. Of course, as is the case with FIG. 6, this image display device can tilt and rotate the moving unit 7 with respect to the base 6B.

In this embodiment, too, the projectors 20, 21 may be disposed so that they face the screen 5, and the image outputted from the projectors may be projected on the screen 5 directly.

As mentioned above, as many apparently widely different embodiments of this invention may be made without departing from the spirit and scope thereof, it is to be understood that the invention is not limited to the specific embodiments thereof except as defined in the appended claims.

The invention claimed is:

1. An image display device comprising:
an image projection means which receives an image signal and outputs an image;
a reflecting mirror which reflects the image outputted from said image projection means;
an image display means having an arbitrarily-shaped projection plane on which the image reflected by said reflecting mirror is projected from a front side;
an image signal processing means which performs a distortion correction to the image signal to be inputted into said image projection means so that the image can be displayed on said projection plane without distortion;
a base for supporting at least said image projection means, said reflecting mirror, and said image display means;
wherein
the image display device is configured to be connected with an external camera to allow an observer to perform a predetermined work while observing the image taken by said external camera on said projection plane,
said image display means having a curved projection plane,
said image signal processing means receiving the image taken by said external camera and performing the distortion correction so that the image taken by said external camera can be displayed on said curved projection plane without distortion,
said image projection means, said reflecting mirror, and said image display means are assembled in one to constitute a single moving unit,
said image display device further comprising a lifting means capable of moving said moving unit in a vertical direction with respect to said base.

2. The image display device as set forth in claim 1, wherein, a view point of the observer is predetermined,
in a x-y coordinate with an x-axis and a y-axis which are defined so that the x-axis is along a line of sight of an observer when looking at said image display means horizontally and the y-axis is along the vertical direction, said reflecting mirror is installed so that a position $(x_M, y_M)$ of a lower end of said reflecting mirror meets the following equation:

$$(y_i-y_0)x_M-(x_i-x_0)y_M \leq x_0 y_i - x_i y_0 \quad \text{(eq.)}$$

where $x_o$ and $y_o$ are x, y coordinates of the predetermined view point, and $x_i$, and $y_i$, are x, y coordinates of a position of an upper end of the projection plane of said image display means.

3. The image display device as set forth in claim 1, wherein said moving unit is configured to be tiltable with respect to said base about an axis which is perpendicular to the vertical direction of the image display unit and is parallel to an aperture plane of said projection plane.

4. The image display device as set forth in claim 1, wherein said moving unit is configured to be rotatable with respect to said base about an axis which is along the vertical direction of the image display unit.

5. The image display device as set forth in claim 1, wherein, said image projection means has a left-eye projector for outputting an image for a left eye and a right-eye projector for outputting an image for a right eye to display a three-dimensional image on said image display means.

6. The image display device as set forth in claim 1, wherein said image projection means, said reflecting mirror, and said image display means are assembled in one using a mounting member, said mounting member being a generally rectangular parallelepiped having a concave portion in one side surface,
said image display means having a concave projection plane, said concave projection plane being disposed in the concave portion of said mounting member.

7. The image display device as set forth in claim 6, wherein said base has a box-shaped housing having an opened upper surface,
a lower part of said mounting member being housed in said housing so as to be freely moved up and down.

8. The image display device as set forth in claim 1, wherein said base is provided with a handrail and wheels so as to be movable.

9. The image display device as set forth in claim 1, wherein said base is configured to be fixed to a ground at one end and to support said moving unit at the other end,
the image display device further comprising a rotating means configured to rotate said moving unit with respect to said base, a tilting means configured to tilt said moving unit with respect to said base, and an expanding means configured to move said moving unit with respect to said base, between said base and said moving unit.

10. An image display device comprising:
an image projection means which receives an image signal and outputs an image;
an image display means having an arbitrarily-shaped projection plane on which the image outputted from said image projection means is projected from a front side;
an image signal processing means which performs a distortion correction to the image signal to be inputted into said image projection means so that the image can be displayed on said projection plane without distortion;
a base for supporting at least said image projection means and said image display means;
wherein
the image display device is configured to be connected with an external camera to allow an observer to perform a predetermined work while observing the image taken by said external camera on said projection plane,
said image display means having a curved projection plane,
said image signal processing means receiving the image taken by said external camera and performing the distortion correction so that the image taken by said external camera can be displayed on said curved projection plane without distortion,
said image projection means and said image display means are assembled in one to constitute a single moving unit,
said image display device further comprising a lifting means capable of moving said moving unit in a vertical direction with respect to said base.

11. The image display device as set forth in claim 10, wherein
said moving unit is configured to be tiltable with respect to said base about an axis which is perpendicular to the vertical direction of the image display unit and is parallel to an aperture plane of said projection plane.

12. The image display device as set forth in claim 10, wherein
said moving unit is configured to be rotatable with respect to said base about an axis which is along the vertical direction of the image display unit.

13. The image display device as set forth in claim 10, wherein,
said image projection means has a left-eye projector for outputting an image for a left eye and a right-eye projector for outputting an image for a right eye to display a three-dimensional image on said image display means.

14. The image display device as set forth in claim 10, wherein
said base is provided with a handrail and wheels so as to be movable.

15. The image display device as set forth in claim 10, wherein
said base is configured to be fixed to a ground at one end and to support said moving unit at the other end,
the image display device further comprising a rotating means configured to rotate said moving unit with respect to said base, a tilting means configured to tilt said moving unit with respect to said base, and an expanding means configured to move said moving unit with respect to said base, between said base and said moving unit.

* * * * *